US012625121B2

(12) United States Patent
Mo et al.

(10) Patent No.: US 12,625,121 B2
(45) Date of Patent: May 12, 2026

(54) GAS DETECTOR

(71) Applicant: SNDWAY TECHNOLOGY (GUANGDONG) CO., LTD., Dongguan (CN)

(72) Inventors: Yeyi Mo, Dongguan (CN); Gang He, Dongguan (CN)

(73) Assignee: SNDWAY TECHNOLOGY (GUANGDONG) CO., LTD., Dongguan (CN)

( * ) Notice: Subject to any disclaimer, the term of this patent is extended or adjusted under 35 U.S.C. 154(b) by 315 days.

(21) Appl. No.: 18/465,176

(22) Filed: Sep. 12, 2023

(65) Prior Publication Data

US 2024/0085392 A1 Mar. 14, 2024

(30) Foreign Application Priority Data

Sep. 14, 2022 (CN) .......................... 202222431811.X

(51) Int. Cl.
| | |
|---|---|
| *G01N 33/00* | (2006.01) |
| *G01M 3/18* | (2006.01) |
| *G01M 3/22* | (2006.01) |
| *G08B 21/16* | (2006.01) |
| *G01N 35/00* | (2006.01) |

(52) U.S. Cl.
CPC .......... *G01N 33/0063* (2013.01); *G01M 3/18* (2013.01); *G01M 3/22* (2013.01); *G01N 33/0047* (2013.01); *G01N 33/0073* (2013.01); *G01N 33/009* (2024.05); *G08B 21/16* (2013.01); *G01N 2035/009* (2013.01)

(58) Field of Classification Search
CPC .......... G01M 3/18; G01M 3/182; G01M 3/22; G01M 3/222; G01N 33/0062; G01N 33/0063; G01N 33/0047; G01N 33/0073; G01N 33/009; G01N 2035/00891; G01N 2035/009; G08B 21/16
See application file for complete search history.

(56) References Cited

U.S. PATENT DOCUMENTS

2003/0079519 A1* 5/2003 Wilkinson ............ G01M 3/205
73/23.2

FOREIGN PATENT DOCUMENTS

| | | | | | |
|---|---|---|---|---|---|
| CN | 204805994 U | * | 11/2015 | ................ | F21S 2/00 |
| CN | 214256484 U | * | 9/2021 | ................ | H04N 7/18 |
| WO | WO-2017177983 A1 | * | 10/2017 | ............. | G01N 27/12 |

* cited by examiner

*Primary Examiner* — Benjamin R Schmitt

(57) ABSTRACT

A gas detector includes a gas detector body; the gas detector body includes a detection probe, a gas detector housing, and a universal shaped tube. An end of the universal shaped tube is connected with the gas detector housing, the other end of the universal shaped tube is connected with the detection probe, and the detection probe is internally integrated with a sensor used to detect a leakage gas, an alarm lamp used for an alarm indication when the leakage gas is detected, and a lighting device used to illuminate. According to the gas detector, an extending portion of the universal shaped tube is provided with the protection probe, and the alarm lamp and the lighting device are added therein, realizing the alarm indication, and being used to illuminate as a searchlight in an area with poor lighting of a gas pipeline during non-alarm.

9 Claims, 4 Drawing Sheets

110

120

130

140

150

160    150

GAS DETECTOR

TECHNICAL FIELD

The disclosure relates to the technical field of gas detection, particularly to a gas detector.

BACKGROUND

Natural gas is usually transported through a gas pipeline, and the gas pipeline may be likely to leak the natural gas due to its aging and other reasons. On the one hand, since the natural gas is a flammable gas, severe fire explosion accidents may be caused when the natural gas leaks. On the other hand, the natural gas is a harmful gas, and casualty accidents may be caused when a large amount of the harmful gas is leaked and inhaled by a person. Therefore, multiple gas detectors are generally used to detect whether a content of the natural gas in the air exceeds a standard safety value.

At present, for conventional gas leak detectors, a sensor is connected to its housing or a sensor is provided with a universal shaped tube used as a probe. However, regardless of the above structures, there is a problem of inconvenient operation in areas with poor lighting.

SUMMARY

Technical Problem to be Solved

In view of the above disadvantages and deficiencies of the related art, the disclosure provides a gas detector, which solves the technical problem that the existing gas detector is inconvenient to operate in the area with poor lighting.

Technical Solution

In order to achieve the above purpose, a main technical solution provided by the disclosure is as follows.

The disclosure provides a gas detector, including a gas detector body; the gas detector body includes a detection probe, a gas detector housing, and a universal shaped tube; an end of the universal shaped tube is connected to the gas detector housing, and another end of the universal shaped tube is connected to the detection probe, and the detection probe is internally integrated with a sensor configured to detect a leakage gas, an alarm lamp configured to indicate an alarm when the leakage gas is detected, and a lighting device configured to illuminate.

In an embodiment of the disclosure, the gas detector housing is provided with a button configured to turn on or turn off the lighting device.

In an embodiment of the disclosure, the gas detector body further includes a first controller, a light-emitting diode (LED) module, and a first drive circuit; the LED module includes the alarm lamp and the lighting device; and the first controller is connected to the LED module through the first drive circuit.

In an embodiment of the disclosure, the first drive circuit includes a first resistor, a second resistor, a third resistor, a fourth resistor, a first triode, and a second triode. The first resistor is connected to a first interface of the first controller and a base electrode of the first triode, an emitter electrode of the first triode is connected to an emitter electrode of the second triode, and a collector electrode of the first triode is connected to the second resistor; the third resistor is connected to a second interface of the first controller and a base electrode of the second triode, and a collector electrode of the second triode is connected to the fourth resistor; and the second resistor and the fourth resistor are connected to the LED module.

In an embodiment of the disclosure, the gas detector body further includes a second drive circuit, and the first controller is connected to the sensor through the second drive circuit.

In an embodiment of the disclosure, the second drive circuit includes a fifth resistor, a sixth resistor, a seventh resistor, a variable resistor, and a first capacitor. The fifth resistor is connected to a third interface of the first controller, an end of the first capacitor, the sixth resistor, and the variable resistor; another end of the first capacitor is grounded; the sixth resistor is connected to the seventh resistor; the seventh resistor is connected to the variable resistor; and the variable resistor is connected to the sensor.

In an embodiment of the disclosure, the gas detector body further includes a third drive circuit and a voice broadcasting device configured to perform voice broadcasting when the leakage gas is detected, and the first controller is connected to the voice broadcasting device through the third drive circuit.

In an embodiment of the disclosure, the third drive circuit includes a second controller, a second capacitor, a third capacitor, a fourth capacitor, a first diode, and a second diode. The second controller is connected to a fourth interface of the first controller, a fifth interface of the first controller, a sixth interface of the first controller, an end of the second capacitor, the voice broadcasting device, an end of the fourth capacitor, an end of the first diode, and an end of the third capacitor; another end of the second capacitor is grounded; another end of the fourth capacitor is connected to the voice broadcasting device; the first diode is connected to the second diode; and another end of the third capacitor is grounded.

In an embodiment of the disclosure, the gas detector body further includes a fourth drive circuit and a motor configured to perform vibration reminding when the leakage gas is detected, and the first controller is connected to the motor through the fourth drive circuit.

In an embodiment of the disclosure, the fourth drive circuit includes a ninth resistor, a tenth resistor, and a field effect transistor. The ninth resistor is connected to a seventh interface of the first controller, the tenth resistor, and a gate electrode of the field effect transistor; the tenth resistor is connected to a source electrode of the field effect transistor; and a drain electrode of the field effect transistor is connected to the motor.

Beneficial Effects

Beneficial effects of the disclosure are as follows. The gas detector provided by the embodiments of the disclosure uses a protruding portion of the universal shaped tube as the detection probe, and adds the alarm lamp and the lighting device within the detection probe. Therefore, the gas detector can not only provide an alarm indication, but also can be used as a searchlight to illuminate the area with poor lighting in the gas pipeline when it is not used for the alarm indication. Furthermore, the gas detector can search for the gas pipeline and accurately position the leaked gas pipeline, thereby solving the problem of inconvenient operation in the area with poor lighting in the related art.

In order to make the above objects, features, and beneficial effects to be implemented in the embodiments of the disclosure more comprehensible, the following detailed description provides illustrated embodiments with reference to attached drawings.

BRIEF DESCRIPTION OF DRAWINGS

In order to more clearly illustrate the technical solution of the embodiments of the disclosure, the attached drawings that need to be used in the embodiments of the disclosure are briefly described below, and it should be understood that the following drawings illustrate only the illustrated embodiments of the disclosure, and therefore should not be considered as limiting the scope of the disclosure.

DETAILED DESCRIPTION OF EMBODIMENTS

In order to better illustrate the disclosure and facilitate understanding, the disclosure is described in detail below through embodiments with reference to attached drawings.

According to a gas detector provided by an embodiment of the disclosure, a protruding portion of a universal shaped tube is used as a detection probe, and an alarm lamp and a lighting device are disposed in the detection probe. Therefore, the gas detector can not only provide an alarm indication, but also can be used as a searchlight to illuminate an area with poor lighting in a gas pipeline and to search for the gas pipeline when it is not used for the alarm indication. Furthermore, the gas detector is conductive to accurate search and positioning of a leaked gas pipeline.

In order to better understand the above technical solution, illustrated embodiments of the disclosure will be described in more detail below with reference to the attached drawings. Although the illustrated embodiments of the disclosure are shown in the attached drawings, it should be understood that the disclosure may be implemented in various forms and should not be limited by the embodiments set forth herein. Rather, the illustrated embodiments are provided in order to be able to understand the disclosure more clearly and thoroughly, and to fully convey the scope of the disclosure to those skilled in the related art.

It should be noted that the herein devices involved in the embodiments of the disclosure are all physical devices, and connection manners involved in the embodiments of the disclosure are also physical connections.

Figure 1A:
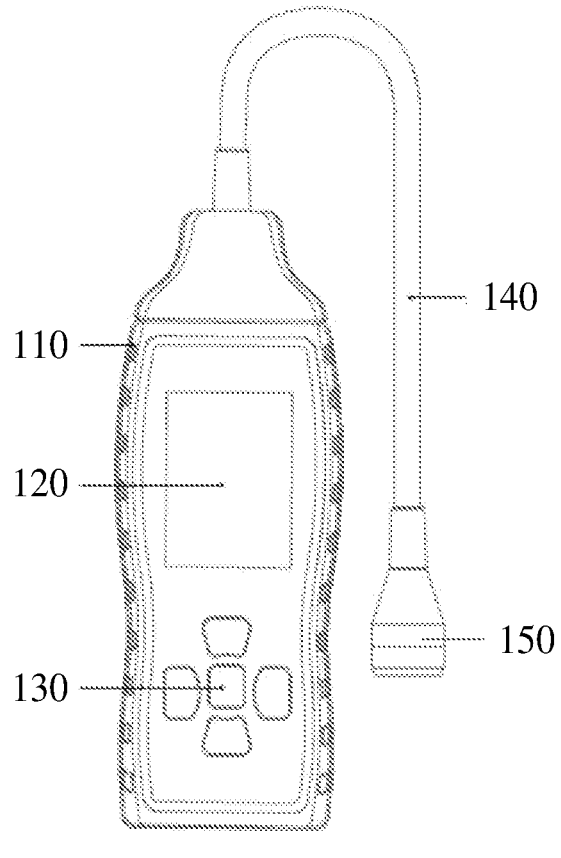
FIG. 1A illustrates a front view of a gas detector according to an embodiment of the disclosure.
Figure 1B:
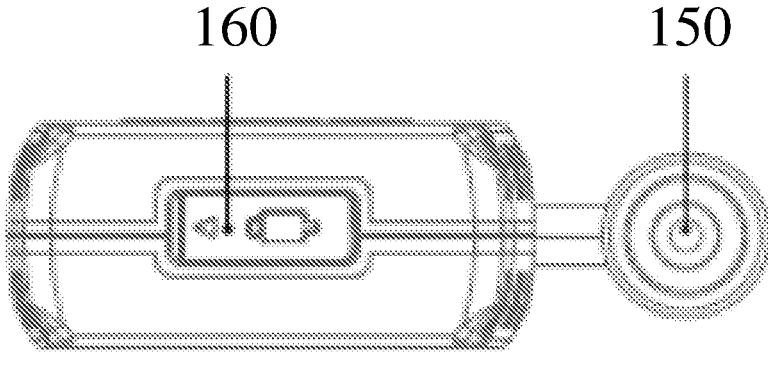
FIG. 1B illustrates a bottom view of the gas detector according to the embodiment of the disclosure.

Referring to FIG. 1A, the gas detector includes a gas detector body; the gas detector body includes a button 130, which is used for turning on or turning off the lighting device (i.e., the lighting device is turned on or turned off under an instruction of the button 130), a display screen 120, a detection probe 150, a gas detector housing 110, and a universal shaped tube 140. The button 130 and the display screen 120 are disposed on an outer surface of the gas detector housing 110, an end of the universal shaped tube 140 is connected to the gas detector housing 110, and the other end of the universal shaped tube 140 is connected to the detection probe 150. Furthermore, the detection probe 150 is internally integrated with a sensor configured to detect a leakage gas, an alarm lamp configured to indicate an alarm when the leakage gas is detected, and a lighting device configured to illuminate (i.e., the universal shaped tube 140, the sensor, the alarm lamp, and the lighting device are integrated as a whole to form the detection probe 150). In addition, in combination with FIG. 1B, the gas detector body further includes a universal serial bus (USB) interface 160.

Figure 2:
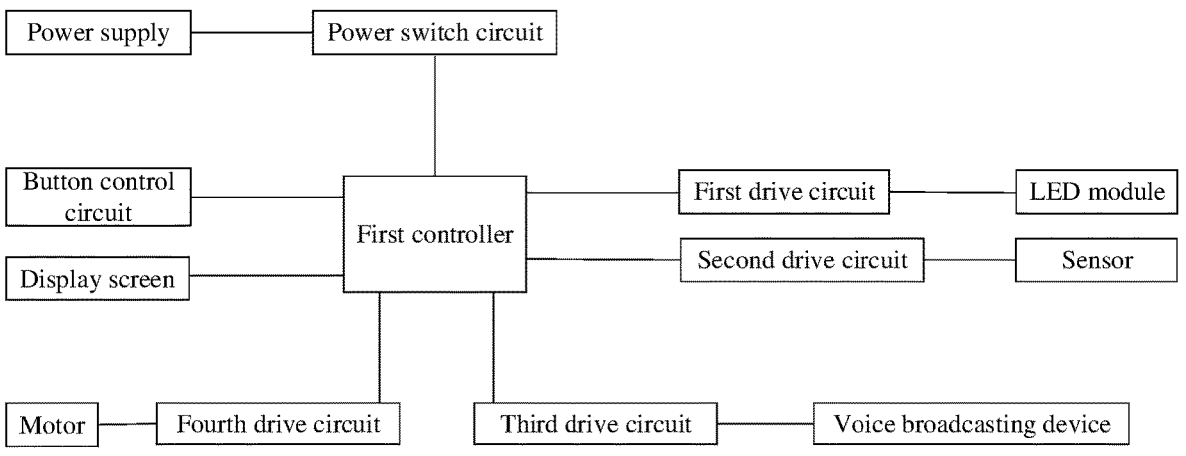
FIG. 2 illustrates a schematic diagram of a gas detector housing according to an embodiment of the disclosure.

Furthermore, referring to FIG. 2, the gas detector body further includes a power supply, a power switch circuit, a first controller, a first drive circuit, a light-emitting diode (LED) module, a second drive circuit, a sensor, a third drive circuit, a voice broadcasting device, a fourth drive circuit, a motor, a display screen, and a button control circuit. The power supply is connected with the power switch circuit; and the first controller is connected with the power switch circuit, the first drive circuit, the second drive circuit, the third drive circuit, the fourth drive circuit, the display screen, and the button control circuit, individually. Furthermore, the first drive circuit is connected with the LED module; the second drive circuit is connected with the sensor; the third drive circuit is connected with the voice broadcasting device; and the fourth drive circuit is connected with the motor.

It should be understood that a specific structure of the power supply can be set according to actual requirements, and the embodiments of the disclosure are not limited thereto.

For example, the power supply may be a lithium battery.

It should also be understood that a specific structure of the power switch circuit can also be set according to actual requirements, and the embodiments of the disclosure are not limited thereto.

For example, the power switch circuit can be an existing power switch circuit.

It should also be understood that a specific structure of the first controller can also be set according to actual requirements, and the embodiments of the disclosure are not limited thereto.

For example, the first controller can be a chip with model STM32F030C8T6.

It should also be understood that a specific structure of the first drive circuit can also be set according to actual requirements, and the embodiments of the disclosure are not limited thereto.

Figure 3:
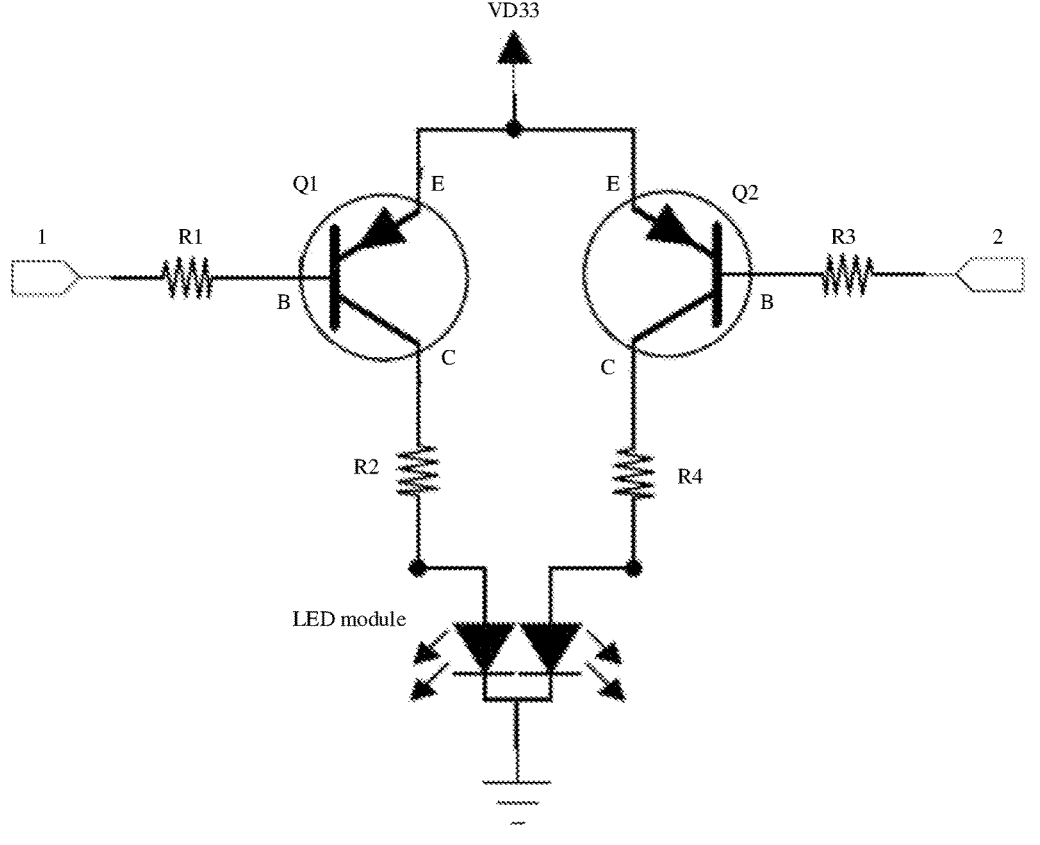
FIG. 3 illustrates a schematic diagram of a first drive circuit according to an embodiment of the disclosure.

In an illustrated embodiment, referring to FIG. 3, the first drive circuit includes a first resistor R1, a second resistor R2, a third resistor R3, a fourth resistor R4, a first triode Q1, and a second triode Q2. The first resistor R1 is connected to a first interface 1 of the first controller and a base electrode B of the first triode Q1, an emitter electrode E of the first triode Q1 is connected to an emitter electrode E of the second triode Q2, and a collector electrode C of the first triode Q1 is connected to the second resistor R2; the third resistor R3 is connected to a second interface 2 of the first controller and a base electrode B of the second triode Q2, and a collector electrode C of the second triode Q2 is connected to the fourth resistor R4; and the second resistor R2 and the fourth resistor R4 are connected to the LED module. In an illustrated embodiment, the LED module includes the alarm lamp and the lighting device.

On the basis of the first drive circuit, when the sensor detects that there is the leakage gas, the sensor outputs signals to the first controller, and when a concentration of the leakage gas reaches a set value, it is displayed in real time through the display screen 120, i.e., the display screen 120 display the concentration of the leakage gas in real time. At the same time, a pin corresponding to the first interface 1 of the first controller and a pin corresponding to the second interface 2 of the first controller are changed from a high level to a low level, and then the two pins are respectively communicated with the first resistor R1 and the third resistor R3, thereby respectively driving the first triode Q1 and the second triode Q2 to be turned on, and turning on the LED module with double color of red and white. In addition, when the gas detector of the disclosure alarms, the LED module with double color of red and white flashes in red (i.e., the alarm lamp flashes in red). Moreover, when the gas detector does not give the alarm, the LED module can be controlled to be turned on in white (i.e., the lighting device illuminates in white) as a flashlight searchlight through the button 130.

It should also be understood that a specific structure of the LED module can also be set according to actual require- ments, and the embodiments of the disclosure are not limited thereto.

For example, the LED module can be an existing module.

It should also be understood that a specific structure of the second drive circuit can also be set according to actual requirements, and the embodiments of the disclosure are not limited thereto.

Figure 4:
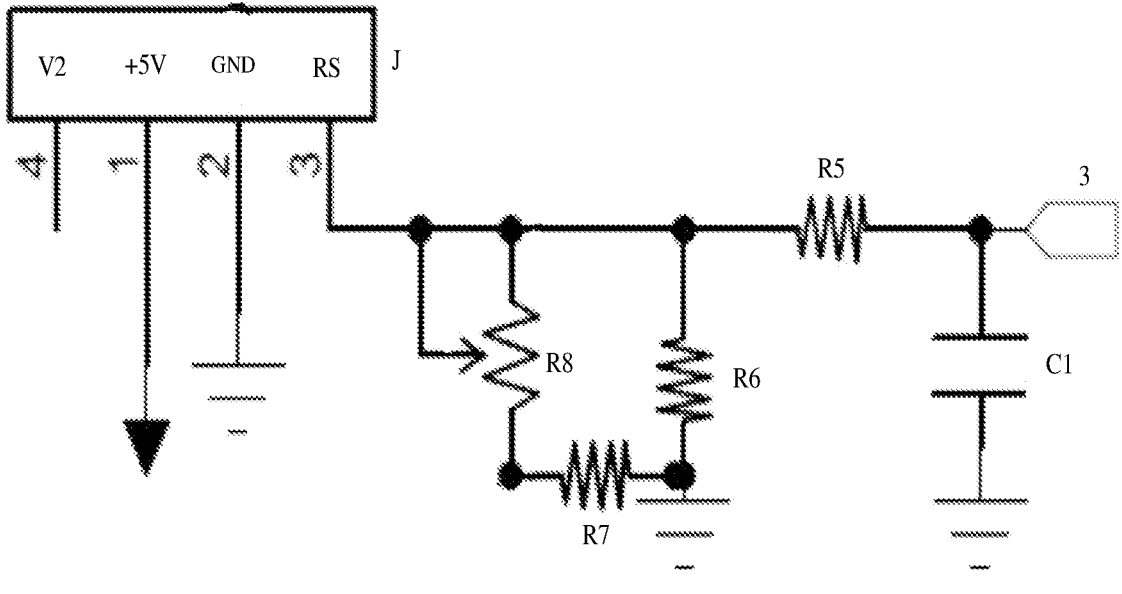
FIG. 4 illustrates a schematic diagram of a second drive circuit according to an embodiment of the disclosure.

In an illustrated embodiment of the disclosure, referring to FIG. 4, the second drive circuit includes a fifth resistor R5, a sixth resistor R6, a seventh resistor R7, a variable resistor R8, and a first capacitor C1. The fifth resistor R5 is con- nected to a third interface 3 of the first controller, an end of the first capacitor C1, the sixth resistor R6, and the variable resistor R8; the other end of the first capacitor C1 is grounded; the sixth resistor R6 is connected to the seventh resistor R7; the seventh resistor R7 is connected to the variable resistor R8; and the variable resistor R8 is con- nected to the sensor.

It should also be understood that a specific structure of the sensor can also be set according to actual requirements, and the embodiments of the disclosure are not limited thereto.

For example, the sensor may be an existing sensor.

It should also be understood that a specific structure of the third drive circuit can also be set according to actual requirements, and the embodiments of the disclosure are not limited thereto.

Figure 5:
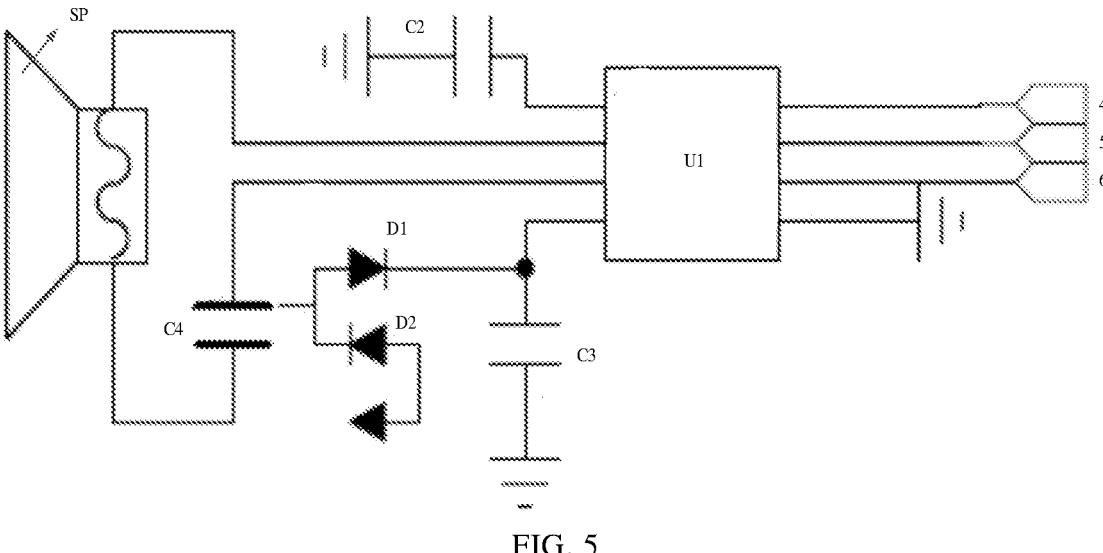
FIG. 5 illustrates a schematic diagram of a third drive circuit according to an embodiment of the disclosure.

For example, referring to FIG. 5, the third drive circuit includes a second controller U1, a second capacitor C2, a third capacitor C3, a fourth capacitor C4, a first diode D1, and a second diode D2. The second controller U1 is con- nected to a fourth interface 4 of the first controller, a fifth interface 5 of the first controller, a sixth interface 6 of the first controller, an end of the second capacitor C2, the voice broadcasting device SP, an end of the fourth capacitor C4, an end of the first diode D1, and an end of the third capacitor C3; the other end of the second capacitor C2 is grounded; the other end of the fourth capacitor C4 is connected to the voice broadcasting device SP; the first diode D1 is connected to the second diode D2; the second diode D2 is connected to the power supply (i.e., a lithium battery); for example, an arrow shown in FIG. 5 illustrates the connection between the power supply and the second diode D2; and the other end of the third capacitor C3 is grounded.

On the basis of the third drive circuit, when the gas detector starts up and alarms, a pin corresponding to the fourth interface 4 of the first controller, a pin corresponding to the fifth interface 5 of the first controller, and a pin corresponding to the sixth interface 6 of the first controller are communicated with the second controller U1 stored with preset voice, thereby realizing voice broadcast and voice alarm.

It should also be understood that a specific structure of the second controller U1 can also be set according to actual requirements, and the embodiments of the disclosure are not limited thereto.

For example, the second controller U1 can be a chip with model SC8120B.

It should also be understood that a specific structure of the voice broadcasting device SP can also be set according to actual requirements, and the embodiments of the disclosure are not limited thereto.

For example, the voice broadcasting device SP can be a speaker.

It should also be understood that a specific structure of the fourth drive circuit can also be set according to actual requirements, and the embodiments of the disclosure are not limited thereto.

Figure 6:
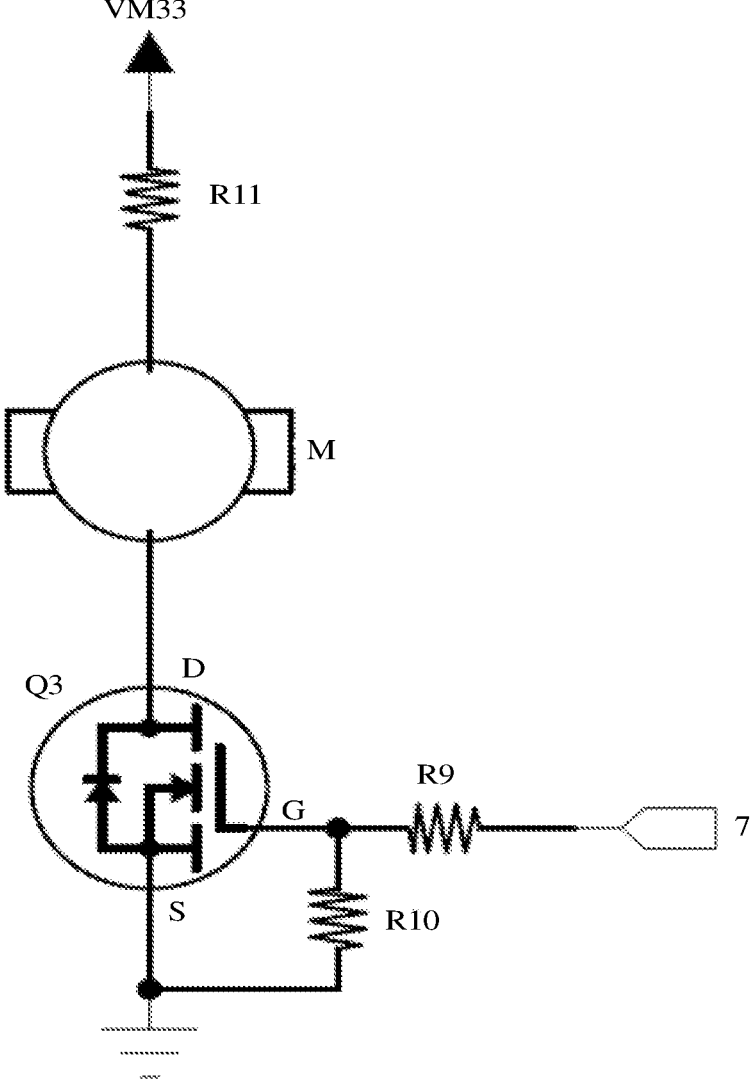
FIG. 6 illustrates a schematic diagram of a fourth drive circuit according to an embodiment of the disclosure.

For example, referring to FIG. 6, the fourth drive circuit includes a ninth resistor R9, a tenth resistor R10, and a field effect transistor Q3. The ninth resistor R9 is connected to a seventh interface 7 of the first controller, the tenth resistor R10, and a gate electrode G of the field effect transistor Q3; the tenth resistor R10 is connected to a source electrode S of the field effect transistor Q3; the source electrode S of the field effect transistor Q3 is grounded; and a drain electrode D of the field effect transistor Q3 is connected to the motor. Furthermore, the motor can be connected to the power supply (i.e., VM33) through an eleventh resistor R11.

On the basis of the fourth drive circuit, when the gas detector of the disclosure starts up and alarms, a pin corre- sponding to the seventh interface 7 of the first controller outputs a high level, and the gas detector body is driven by vibrating the motor therein through the ninth resistor R9 and the tenth resistor R10, thereby achieving the vibration alarm.

It should also be understood that a specific structure of the motor can also be set according to actual requirements, and the embodiments of the disclosure are not limited thereto.

For example, the motor can be an existing motor.

It should be noted here that the specific values of the elements involved in the gas detector can be set according to actual requirements, and the embodiments of the disclosure are not limited thereto.

For example, the first resistor R1 is 1.2K ohms (also referred to 1,200 ohms); and for example, the third resistor R3 is 1.2K ohms, etc.

Therefore, according to the gas detector provided by the embodiments of the disclosure, the extending portion of the universal shaped tube 140 is used as the detection probe 150, and the alarm lamp and the lighting device are added within the detection probe 150, thereby realizing the alarm indica- tion, and realizing the illumination as the searchlight in the area with poor lighting of the gas pipeline during non-alarm. Furthermore, the gas detector of the disclosure can search and find the gas pipeline, and facilitate accurate search and positioning of the leaked gas pipeline.

In addition, the gas detector can also supply power through a large-capacity lithium battery, thereby providing a longer standby test time, and providing functions such as voice broadcasting and voice alarming.

It should be understood that the above-mentioned gas detector is merely illustrative, and those skilled in the related art can perform various deformation according to the above- mentioned method, and the modification or deformation is also within the scope of the protection of the disclosure.

In the description of the disclosure, it should be understood that terms "first" and "second" are used for descriptive purposes only and cannot be understood as indicating or implying relative importance or implicitly indicating the number of indicated technical features. Thus, the features defined with "first" and "second" may explicitly or implicitly include one or more of the features. In the description of the disclosure, "a plurality of" means two or more, unless specifically defined otherwise.

In the disclosure, terms such as "mounted", "connected to", "connected with", "fixed", etc. should be construed broadly unless expressly specified and defined otherwise. For example, the connection may be a fixed connection, a detachable connection, or integration; or may be a mechanical connection or an electrical connection; or may be a direct connection or an indirect connection through an intermediate medium; or may be a communication relationship between two elements or an interaction relationship between the two elements. For those skilled in the related art, they can understand the specific meanings of the above terms in the disclosure according to specific situations.

In the disclosure, unless expressly specified and defined otherwise, the first feature is "on" or "under" the second feature, which may be a direct contact between the first feature and the second feature, or the first feature and the second feature are indirectly in contact with each other through an intermediate medium. Moreover, the first feature is "above", "on" and "upper" relative to the second feature, which may be that the first feature is directly above or obliquely above the second feature, or merely indicates that a level height of the first feature is higher than that of the second feature. The first feature is "below", "under" and "lower" relative to the second feature, which may be that the first feature is directly below or obliquely below the second feature, or merely indicates that a level height of the first feature level is lower than that of the second feature.

In the description of the specification of the disclosure, the terms "an embodiment", "some embodiments", "the embodiment", "an example", "an illustrated example", or "some examples" refer to the specific features, structures, materials, or characteristics described in connection with the embodiment or example being included in at least one embodiment or example of the disclosure. In the specification of the disclosure, the schematic representation of the above terms does not necessarily refer to the same embodiment or example. Furthermore, the specific features, structures, materials, or characteristics described may be combined in any suitable manner in any one or more embodiments or examples. In addition, in the case of no contradiction, those skilled in the related art may randomly combine the different embodiments or examples described in the specification as well as the features of different embodiments or examples.

Although the embodiments of the disclosure have been shown and described above, it can be understood that the foregoing embodiments are illustrative and cannot be understood as limitations to the disclosure and those skilled in the related art may make modifications, amendments, substitutions, and variations to the above embodiments within the scope of the disclosure.

What is claimed is:

1. A gas detector, comprising a gas detector body, wherein the gas detector body comprises a detection probe (150), a gas detector housing (110), and a universal shaped tube (140);

wherein an end of the universal shaped tube (140) is connected to the gas detector housing (110), and another end of the universal shaped tube (140) is connected to the detection probe (150), and the detection probe (150) is internally integrated with a sensor configured to detect a leakage gas, an alarm lamp configured to indicate an alarm when the leakage gas is detected, and a lighting device configured to illuminate;

wherein the gas detector body further comprises a first controller, a light-emitting diode (LED) module, and a first drive circuit; the LED module comprises the alarm lamp and the lighting device; and the first controller is connected to the LED module through the first drive circuit;

wherein the gas detector body further comprises a third drive circuit and a voice broadcasting device (SP) configured to perform voice broadcasting when the leakage gas is detected, and the first controller is connected to the voice broadcasting device through the third drive circuit;

wherein the third drive circuit comprises a second controller (U1), a second capacitor (C2), a third capacitor (C3), a fourth capacitor (C4), a first diode (D1), and a second diode (D2); and wherein the second controller (U1) is connected to a fourth interface (4) of the first controller, a fifth interface (5) of the first controller, a sixth interface (6) of the first controller, an end of the second capacitor (C2), the voice broadcasting device (SP), an end of the fourth capacitor (C4), an end of the first diode (D1), and an end of the third capacitor (C3); another end of the second capacitor (C2) is grounded; another end of the fourth capacitor (C4) is connected to the voice broadcasting device (SP); the first diode (D1) is connected to the second diode (D2); and another end of the third capacitor (C3) is grounded.

2. The gas detector as claimed in claim 1, wherein the gas detector housing (110) is provided with a button (130) configured to turn on or turn off the lighting device.

3. The gas detector as claimed in claim 1, wherein the first drive circuit comprises a first resistor (R1), a second resistor (R2), a third resistor (R3), a fourth resistor (R4), a first triode (Q1), and a second triode (Q2); and wherein the first resistor (R1) is connected to a first interface (1) of the first controller and a base electrode (B) of the first triode (Q1), an emitter electrode (E) of the first triode (Q1) is connected to an emitter electrode (E) of the second triode (Q2), and a collector electrode (C) of the first triode (Q1) is connected to the second resistor (R2); the third resistor (R3) is connected to a second interface (2) of the first controller and a base electrode (B) of the second triode (Q2), and a collector electrode (C) of the second triode (Q2) is connected to the fourth resistor (R4); and the second resistor (R2) and the fourth resistor (R4) are connected to the LED module.

4. The gas detector as claimed in claim 1, wherein the gas detector body further comprises a second drive circuit, and the first controller is connected to the sensor through the second drive circuit.

5. The gas detector as claimed in claim 4, wherein the second drive circuit comprises a fifth resistor (R5), a sixth resistor (R6), a seventh resistor (R7), a variable resistor (R8), and a first capacitor (C1); and wherein the fifth resistor (R5) is connected to a third interface (3) of the first controller, an end of the first capacitor (C1), the sixth resistor (R6), and the variable resistor (R8); another end of the first capacitor (C1) is grounded; the sixth resistor (R6) is connected to the seventh resistor (R7); the seventh resistor (R7) is connected to the variable resistor (R8); and the variable resistor (R8) is connected to the sensor.

6. The gas detector as claimed in claim 1, wherein the gas detector body further comprises a fourth drive circuit and a motor configured to perform vibration reminding when the leakage gas is detected, and the first controller is connected to the motor through the fourth drive circuit.

7. The gas detector as claimed in claim 6, wherein the fourth drive circuit comprises a ninth resistor (R9), a tenth resistor (R10), and a field effect transistor (Q3); and wherein the ninth resistor (R9) is connected to a seventh interface (7) of the first controller, the tenth resistor (R10), and a gate electrode (G) of the field effect transistor (Q3); the tenth resistor (R10) is connected to a source electrode(S) of the field effect transistor (Q3); and a drain electrode (D) of the field effect transistor (Q3) is connected to the motor.

8. A gas detector, comprising:

a gas detector housing (110), a universal shaped tube (140), connected to the gas detector housing (110);

a detection probe (150), connected to an end of the universal shaped tube (140) facing away from the gas detector housing (110);

a first controller, disposed in the gas detector housing (110);

a first drive circuit, disposed in the gas detector housing (110) and electrically connected to the first controller;

a LED module, disposed in the detection probe (150) and electrically connected to the first drive circuit; wherein the LED module is configured to provide at least one of alarm and illumination;

a second drive circuit, disposed in the gas detector housing (110) and electrically connected to the first controller;

a sensor, disposed in the detection probe (150) and electrically connected to the second drive circuit; wherein the sensor is configured to detect a leakage gas;

a third drive circuit, disposed in the gas detector housing (110) and electrically connected to the first controller;

a voice broadcasting device (SP), disposed in the gas detector housing (110) and electrically connected to the third drive circuit; wherein the voice broadcasting device (SP) is configured to perform voice broadcasting when the leakage gas is detected;

a fourth drive circuit, disposed in the gas detector housing (110) and electrically connected to the first controller; and a motor, disposed in the gas detector housing (110) and electrically connected to the fourth drive circuit; wherein the motor is configured to perform vibration reminding when the leakage gas is detected;

wherein the first drive circuit comprises a first resistor (R1), a second resistor (R2), a third resistor (R3), a fourth resistor (R4), a first triode (Q1), and a second triode (Q2); the first resistor (R1) is connected to the first controller and a base electrode (B) of the first triode (Q1), an emitter electrode (E) of the first triode (Q1) is connected to an emitter electrode (E) of the second triode (Q2); a collector electrode (C) of the first triode (Q1) is connected to the second resistor (R2); the third resistor (R3) is connected to the first controller and a base electrode (B) of the second triode (Q2); a collector electrode (C) of the second triode (Q2) is connected to the fourth resistor (R4); and the second resistor (R2) and the fourth resistor (R4) are connected to the LED module;

wherein the second drive circuit comprises a fifth resistor (R5), a sixth resistor (R6), a seventh resistor (R7), a variable resistor (R8), and a first capacitor (C1); the fifth resistor (R5) is connected to the first controller, an end of the first capacitor (C1), the sixth resistor (R6), and the variable resistor (R8); another end of the first capacitor (C1) is grounded; the sixth resistor (R6) is connected to the seventh resistor (R7); the seventh resistor (R7) is connected to the variable resistor (R8); and the variable resistor (R8) is connected to the sensor;

wherein the third drive circuit comprises a second controller (U1), a second capacitor (C2), a third capacitor (C3), a fourth capacitor (C4), a first diode (D1), and a second diode (D2); the second controller (U1) is connected to the first controller, an end of the second capacitor (C2), the voice broadcasting device (SP), an end of the fourth capacitor (C4), an end of the first diode (D1), and an end of the third capacitor (C3); another end of the second capacitor (C2) is grounded; another end of the fourth capacitor (C4) is connected to the voice broadcasting device (SP); the first diode (D1) is connected to the second diode (D2); and another end of the third capacitor (C3) is grounded; and wherein the fourth drive circuit comprises a ninth resistor (R9), a tenth resistor (R10), and a field effect transistor (Q3); the ninth resistor (R9) is connected to the first controller, the tenth resistor (R10), and a gate electrode (G) of the field effect transistor (Q3); the tenth resistor (R10) is connected to a source electrode(S) of the field effect transistor (Q3); and a drain electrode (D) of the field effect transistor (Q3) is connected to the motor.

9. A gas detector, comprising a gas detector body, wherein the gas detector body comprises a detection probe (150), a gas detector housing (110), and a universal shaped tube (140);

wherein an end of the universal shaped tube (140) is connected to the gas detector housing (110), and another end of the universal shaped tube (140) is connected to the detection probe (150), and the detection probe (150) is internally integrated with a sensor configured to detect a leakage gas, an alarm lamp configured to indicate an alarm when the leakage gas is detected, and a lighting device configured to illuminate;

wherein the gas detector body further comprises a first controller, a light-emitting diode (LED) module, and a first drive circuit; the LED module comprises the alarm lamp and the lighting device; and the first controller is connected to the LED module through the first drive circuit;

wherein the gas detector body further comprises a fourth drive circuit and a motor configured to perform vibration reminding when the leakage gas is detected, and the first controller is connected to the motor through the fourth drive circuit;

wherein the fourth drive circuit comprises a ninth resistor (R9), a tenth resistor (R10), and a field effect transistor (Q3); and wherein the ninth resistor (R9) is connected to a seventh interface (7) of the first controller, the tenth resistor (R10), and a gate electrode (G) of the field effect transistor (Q3); the tenth resistor (R10) is connected to a source electrode(S) of the field effect transistor (Q3);

and a drain electrode (D) of the field effect transistor (Q3) is connected to the motor.

* * * * *